United States Patent
Correa et al.

[19]

[11] Patent Number: 6,119,694
[45] Date of Patent: Sep. 19, 2000

[54] NASAL MASK AND HEADGEAR

[75] Inventors: José Luis Correa, North Bergen; Diego Fontayne, Teaneck, both of N.J.; Karl Dallas Kirk, III; James T. Collins, III, both of New York, N.Y.

[73] Assignee: Respironics Georgia, Inc., Marietta, Ga.

[21] Appl. No.: 08/899,806

[22] Filed: Jul. 24, 1997

[51] Int. Cl.$^7$ ................................................ A63B 18/02
[52] U.S. Cl. ............................... 128/207.13; 128/207.18
[58] Field of Search ................ 128/206.18, 206.26, 128/207.13, 207.18

[56] References Cited

U.S. PATENT DOCUMENTS

| | | | |
|---|---|---|---|
| Re. 35,339 | 10/1996 | Rapoport | 128/204.18 |
| 1,192,186 | 7/1916 | Greene | 128/207.13 |
| 1,486,290 | 3/1924 | Littaver | 128/207.13 |
| 3,776,244 | 12/1973 | Morgan | 132/46 |
| 4,149,540 | 4/1979 | Hasslinger | 128/327 |
| 4,354,488 | 10/1982 | Bartos | 128/205.25 |
| 4,641,647 | 2/1987 | Behan | 128/207.18 |
| 4,665,566 | 5/1987 | Garrow | 2/171 |
| 4,741,054 | 5/1988 | Mattes | 2/421 |
| 4,766,610 | 8/1988 | Mattes | 2/6 |
| 4,915,105 | 4/1990 | Lee | 128/206.18 |
| 5,038,776 | 8/1991 | Harrison et al. | 128/207.11 |
| 5,069,205 | 12/1991 | Urso | 128/201.24 |
| 5,074,297 | 12/1991 | Venegas | 128/204.18 |
| 5,243,971 | 9/1993 | Sullivan et al. | 128/207.13 |
| 5,272,772 | 12/1993 | Hahn | 2/195.2 |
| 5,517,986 | 5/1996 | Starr et al. | 128/206.24 |
| 5,526,806 | 6/1996 | Sansoni | 128/207.18 |
| 5,657,752 | 8/1997 | Landis et al. | 128/207.13 |
| 5,746,201 | 5/1998 | Kidd | 128/207.13 |

FOREIGN PATENT DOCUMENTS

| | | | |
|---|---|---|---|
| 2 268 388 | 12/1994 | United Kingdom | A42B 7/00 |
| 9818514 | 5/1998 | WIPO | 128/207.18 |
| WO 98/18541 | 5/1998 | WIPO . | |

OTHER PUBLICATIONS

U.S. Patent application No. 08/741,524, filed Oct. 31, 1996.

*Primary Examiner*—Aaron J. Lewis
*Attorney, Agent, or Firm*—Troutman Sanders LLP; Gerald R. Boss, Esq.

[57] ABSTRACT

A nasal mask assembly having a nare seal for enclosing the nares of a patient and a pair of lateral support members for engaging the cheekbones of a patient and supporting the nasal mask assembly. An associated headgear assembly constructed of semi-rigid members are selectively interconnected for defining a headgear. The nasal mask assembly is interconnected with depending arms of the headgear assembly by contact connectors enabling the nasal mask to be adjusted linearly and angularly with respect to the headgear assembly.

2 Claims, 4 Drawing Sheets

NASAL MASK AND HEADGEAR

BACKGROUND OF THE INVENTION

1. Field of the Invention

This invention relates generally to a nasal mask for providing pressurized gas to a patient and more particularly to a nasal mask which only encloses the nares of a patient which utilizes a pair of lateral support arms which in combination with an associated headgear support the mask.

2. Description of the Related Art

Masks are used for various reasons. Typically masks are interconnected with a source of breathable fluid to be inhaled by a patient. These masks are used for anesthesia and also for providing positive air pressure to a patient in the treatment of obstructive sleep apnea. In the treatment of obstructive sleep apnea, positive air pressure is provided to a patient while the patient is sleeping.

Accordingly, in the treatment of obstructive sleep apnea, mask comfort is important to ensure that the patient may sleep and also to ensure that the patient complies with the treatment. For the treatment of obstructive sleep apnea, the mask must provide a sufficient seal to enable pressure to be maintained within the airway of the patient. Typical masks are bulbous and enclose a large portion of the nose and engage the face of the patient. These masks tend to produce a claustrophobic effect on the patient. Furthermore, these masks generally irritate the bridge of the nose and parts of the patient's face hindering patient comfort.

Also, generally these masks are secured to a patient's head by straps to ensure that a tight seal is had, thus further presenting pressure onto the patient's nose. Additionally, the positioning and securing of the mask with the straps is cumbersome and time consuming. U.S. Pat. No. 5,517,986 illustrates a headgear assembly for a gas delivery mask utilizing straps.

Some masks have been developed which are not bulbous nor fit on a patient's nose, but consist of a pair of elongated flange members which are inserted directly into the patient's nares. U.S. Pat. No. 5,042,478 discloses such a mask. While this type of mask is suitable for its intended purpose, the presentation of air directly into the patient's nares is awkward and generally uncomfortable to the patient.

SUMMARY OF THE INVENTION

Accordingly, it is an object of the present invention to provide a nasal mask which is comfortable to wear by a patient and which is easily secured for providing a seal around the nares of a patient.

Furthermore, it is an object of the present invention to provide a nasal mask which solely encloses the nares of a patient.

Also, it is an object of the present invention to provide a nasal mask and headgear assembly which is easy to position onto a patient and which is adjustable to accommodate the physical characteristics of an individual patient.

Additionally, it is an object of the present invention to provide a nasal mask assembly which matingly adapts to the cheeks of a patient which in combination with a headgear assembly supports the mask.

These objects are achieved, at least in part, by providing a nasal mask assembly for providing gas from a gas source to a patient that includes a nare seal having a surface for encircling the nares of a patent. The nare seal defines a gas opening permitting gas from the gas source to enter into the nares of a patient. A nare seal support carries the nare seal. In a further embodiment of the present invention, the nare seal support includes a pair of leteral arms for engaging the patient's face.

DESCRIPTION OF THE DRAWING

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF THE PREFERRED EMBODIMENT

Now reference will be made with respect to the drawings for understanding of the preferred embodiment of the invention.

Figure 1:
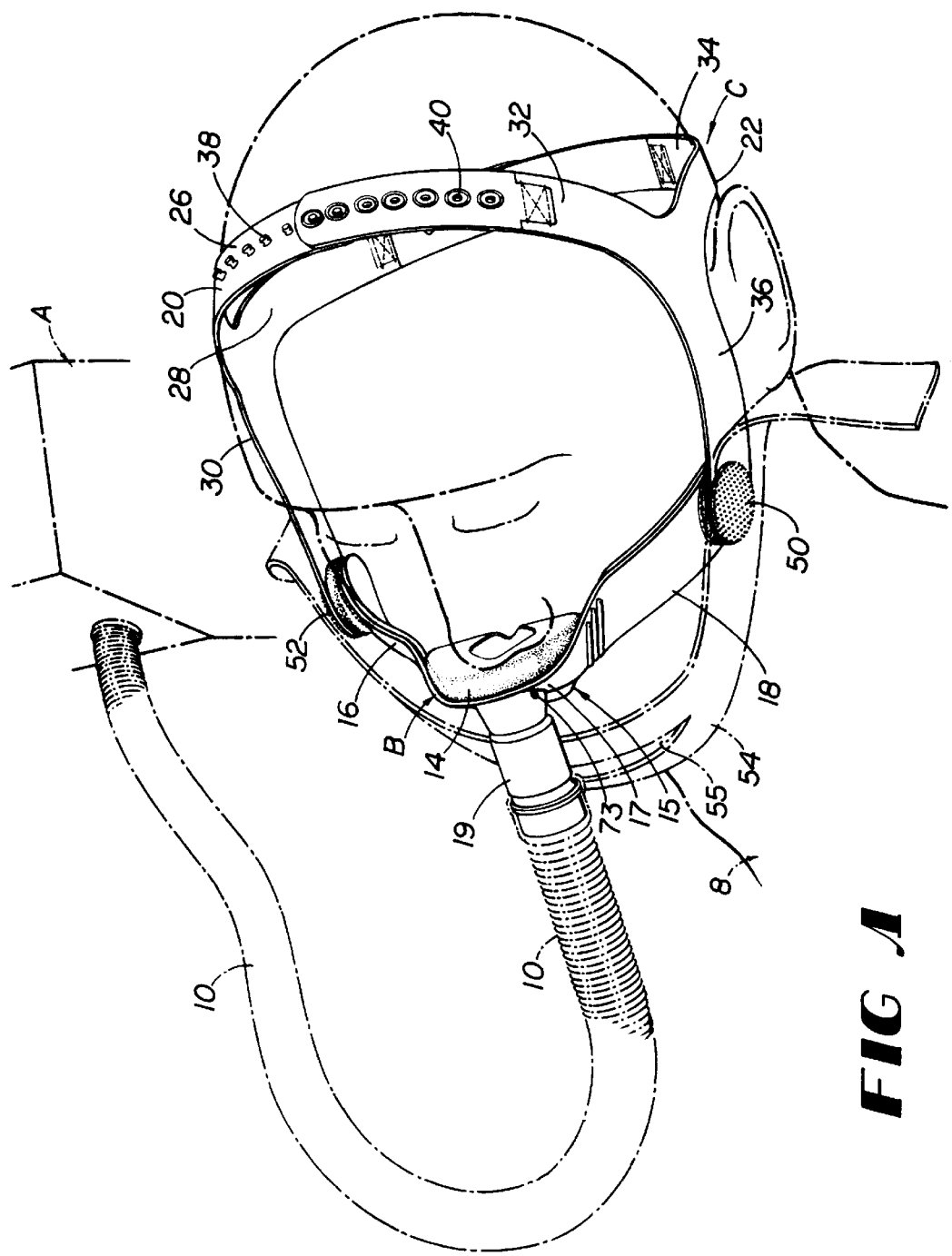
FIG. 1 is a top perspective view of a patient utilizing a nasal mask assembly and headgear assembly according to the present invention.

As shown in FIG. 1, a positive pressure device A provides gas under positive pressure to a patient 8 through a conduit 10. Conduit 10 is in fluid communication with nasal mask assembly B which provides the pressurized gas to the nares of the patient. Headgear assembly C maintains the positioning of nasal mask assembly B with the patient's nares. In this manner, the patient's vision is not obstructed.

Figure 2:
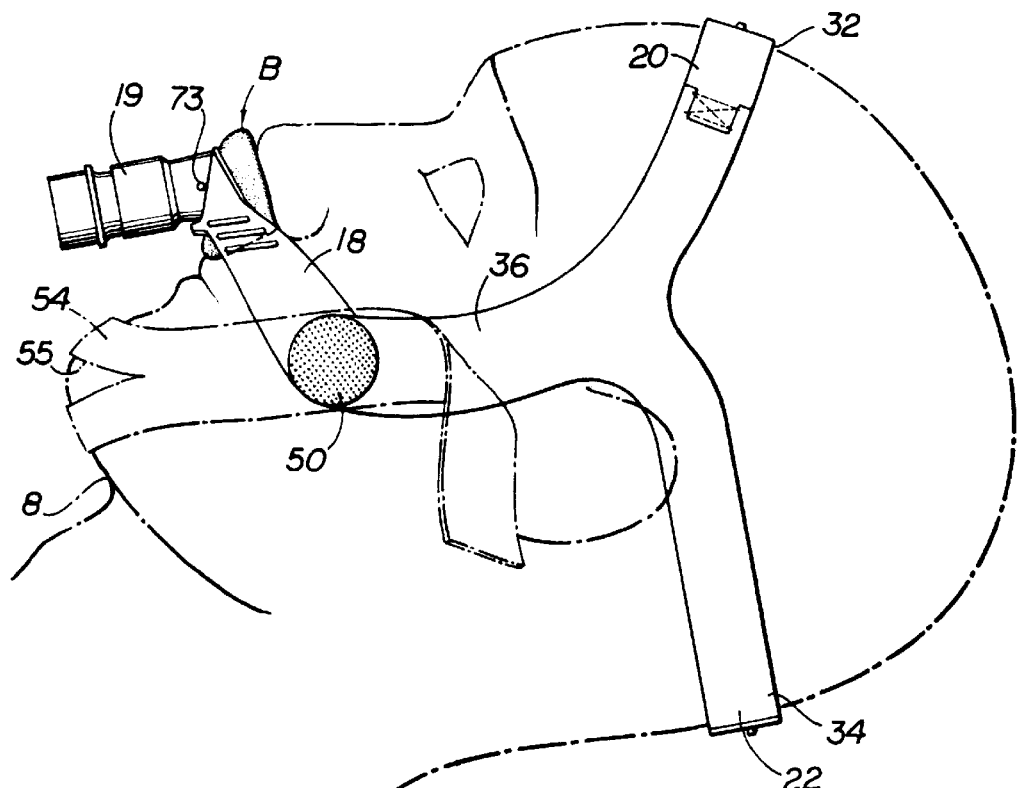
FIG. 2 is a side perspective view of a patient utilizing the nasal mask assembly and headgear assembly according to the present invention.

As shown in FIGS. 1 and 2, nasal mask assembly B includes flexible nare seal 14 and nare seal support 15. Nare seal 14 seals the nares of the patient when positive pressure is applied to nasal mask assembly B. Nare seal support 15 includes first and second support arms 16 and 18 which extend outwardly from central support 17. First and second support arms 16 and 18 preferably traverse the face of the patient and rest against the cheekbones of the patient. In this manner, the force required to maintain a tight seal between nare seal 14 and the nares of the patient are transferred to a sturdy bone structure. A conduit receptor 19 attaches to conduit 10 for communicating pressurized gas from the conduit into the interior of nare seal 14.

As further shown in FIGS. 1 and 2, nasal mask assembly B is secured to headgear assembly C. Headgear assembly C includes first headgear member 20 and second headgear member 22 which are interconnected to define a support structure for supporting nasal mask assembly B in fluid communication with the patient's nares. First headgear member 20 and second headgear member 22 are preferably mirror images. First headgear member 20 is generally "Y" shaped having a first forward lateral arm 26 and a first rearward lateral arm 28 disposed rearwardly of forward lateral arm 26. First headgear member 20 also includes first depending arm 30. In the preferred embodiment, first forward lateral arm 26, first rearward lateral arm 28 and first depending arm 30 are of a unitary construction such that first depending arm 30 depends downward from the junction of forward lateral arm 26 with rearward lateral arm 28. Second headgear member 22, being of a mirror image of first headgear member 20, includes second forward lateral arm 32, second rearward lateral arm 34 and second depending arm 36 and is also preferably of unitary construction.

First and second headgear members are designed to matingly attach to one another. In this manner, first and second headgear members are assembled such that first and second forward lateral arms 26 and 32 encircle the forehead of the patient while first and second rearward lateral arms 28 and 34 encircle the sides and back of the patient's head. First and second depending arms 30 and 36 depend downward along the patient's head in front of the patient's ears. Also, when first and second headgear members 20 and 22 are assembled, they define head opening 45 which receives the crown of the patient leaving a predominant portion of the patient's head unencumbered.

In the preferred embodiment, first forward lateral arm 26 includes pegs 38 and second forward lateral arm 32 includes peg receptacles 40. Also, first rearward lateral arm 28 includes peg receptacles 42 and second rearward lateral arm 34 includes pegs 44 enabling first and second headgear members 20 and 22 to be selectively interconnected depending on the head parameters of the patient to provide a secure fit. By providing sufficient interconnecting elements, headgear assembly C may be constructed to fit an adult, child or even an infant. Furthermore, first and second headgear members 20 and 22 are formed from a semi-rigid plastic material providing a semi-rigid support. The semi-rigid support retains its shape when assembled and transfers support forces along the entire periphery of headgear assembly C.

Figure 3:
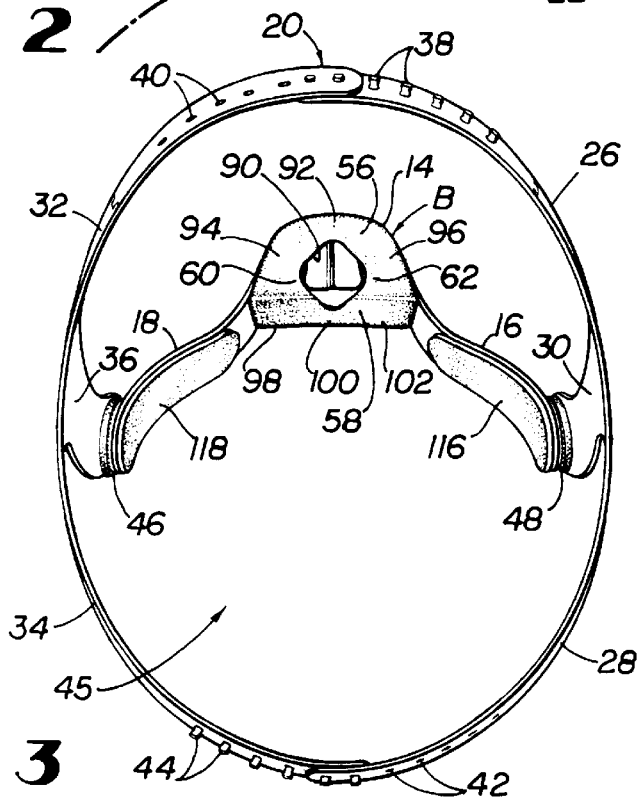
FIG. 3 is a rear view of the nasal mask assembly and headgear assembly according to the present invention.
Figure 4:
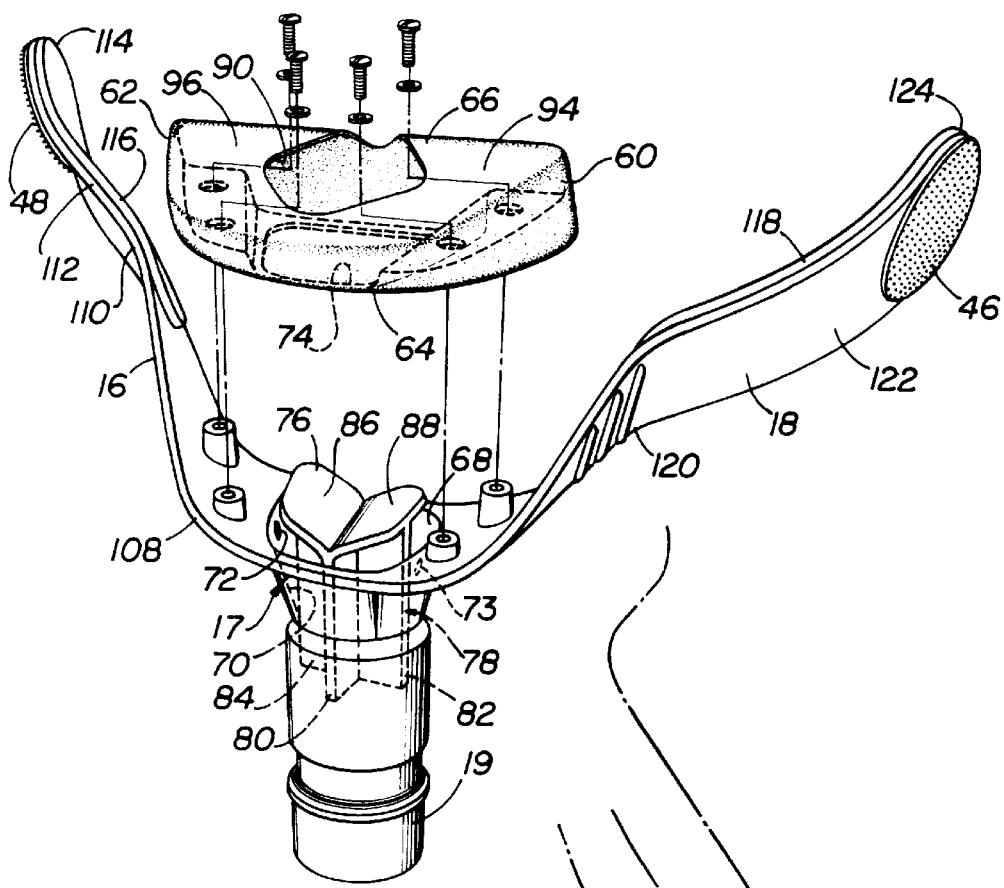
FIG. 4 is an exploded view of the nasal mask assembly according to the present invention.

As further shown in FIGS. 3 and 4, nasal mask assembly B attaches to headgear assembly C via contact connectors 46 and 48. Preferably, contact connectors 46 and 48 include hook and loop fasteners such as Velcro trademark with a respective member being attached to the inside surface of first and second depending arms 30 and 36 and a correspondingly mating member attached to the exterior of support arms 16 and 18. In this manner, support arms 16 and 18 of nasal mask assembly B may be readily attached linearly and at any angle with respect to headgear assembly C for cooperating with the physical characteristics of the patient. Also, since headgear assembly C is semi-rigid and retains its shape, removal of the mask may be achieved by merely releasing either first or second support arm 16 or 18 from its respective mating attachment of the respective first or second depending arm. Strap connectors 50 and 52 attach support strap 54 to headgear assembly C. Support strap 54 includes slit 55 and may be positioned under the chin of the patient or encircling the scalp. Strap connectors 50 and 52 preferably include hook fasteners such as Velcro trademark and matingly engage support strap 54 which is preferably assembled from the fastening component of Velcro trademark.

As shown in FIGS. 2, 3, 4, 5, 5A, 6 and 7, nare seal 14 is a soft membrane preferably made from a material identified as HSIIRTV manufactured by Dow Corning. Nare seal 14 has a top surface 56 which is preferably sloped for engaging the lower portion of a patient's nose including the nostrils. Nare seal 14 also includes a rearward side surface 58 which is generally perpendicular with top surface 56 for engaging the portion of a patient between the patient's mouth and nose which will be hereinafter referenced as the "upper lip". Nare seal 14 also includes left nasal seal side 60, right nasal seal side 62 and nasal seal bottom 64 which in combination with top surface 56 and rearward side surface 58 define nasal seal interior 66.

As shown in FIGS. 4, 5A, 6 and 7, central support 17 defines central orifice 68 which communicates with hollow bore 70. Bias ports 72 and 73 are defined within the interior wall of bore 70 on opposing sides. Nasal seal bottom 64 defines air opening 74. Nare seal 14 is mounted onto nare seal support 15 such that air opening 74 encircles central orifice 68. Bore 70 communicates with conduit receptor 19 to create a gas passageway enabling gas from positive pressure device A to enter into nare seal interior 66 and ultimately breathed by a patient. Gas deflector 76 is positioned within the interior of bore 70 for deflecting gas received by conduit connector into nare seal interior. Gas deflector 76 includes stem 78 having opposing flanges 80, 82, 84 which is received by bore interior 70 and laterally opposing deflecting wings 86 and 88 which extend into nare seal interior. Gas deflector 76 deflects the gas from the positive pressure source into nare seal interior so that the gas encircles the patient's nares to provide a comfortable breathing environment.

Top surface 56 and rearward side surface 58 define orifice 90 which encircles the nares of the patient when gas is supplied under positive pressure. Orifice 90 is preferably diamond shaped and centrally located on top surface 56 and rearward side surface 58 such that a front portion 92 of top surface 56 engages the bottom tip of a patient's nose while left and right side portions 94 and 96 of top surface 56 engages the sides of a patient's nostrils and bottom and left and right side portions 98, 100 and 102 of rearward side surface 58 engage the upper lip of the patient for sealing nare seal 14 around the patient's nares.

Figure 5:
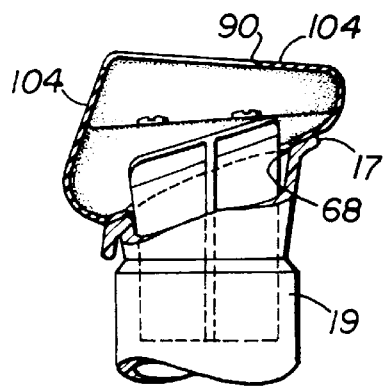
FIG. 5 is side view illustrating the pre inflation position of the nare seal according to the present invention.
Figure 5A:
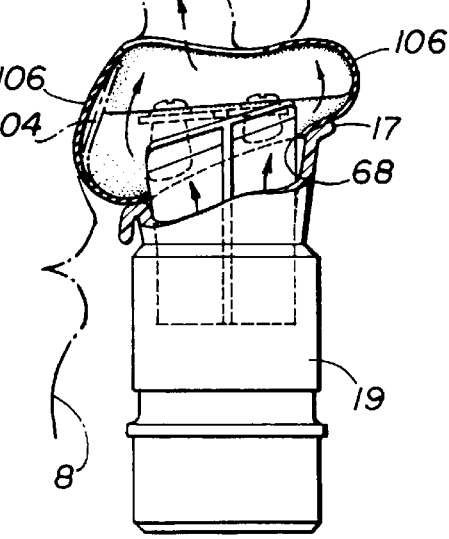
FIG. 5A is an operational view illustrating the pre and post inflation positions of the nasal mask with respect to a patient nares.
Figure 6:
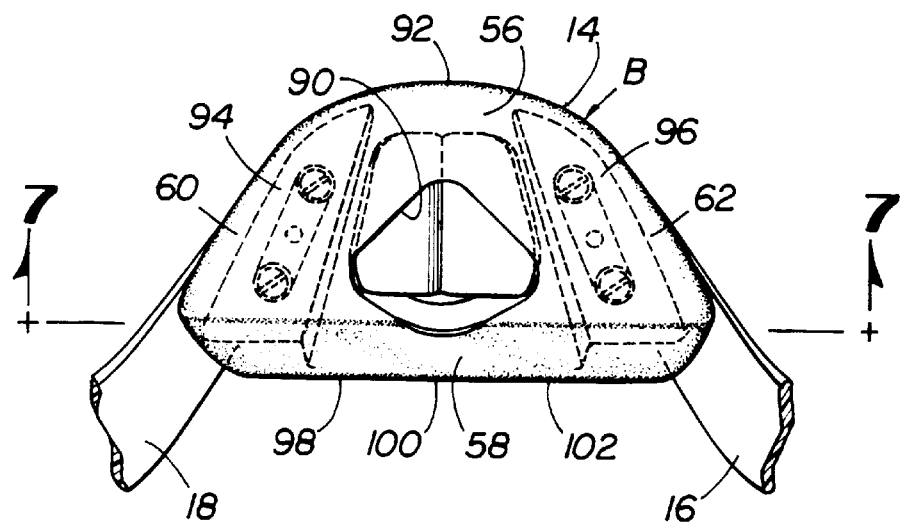
FIG. 6 is a rear prospective view of the nasal mask assembly according to the present invention.
Figure 7:
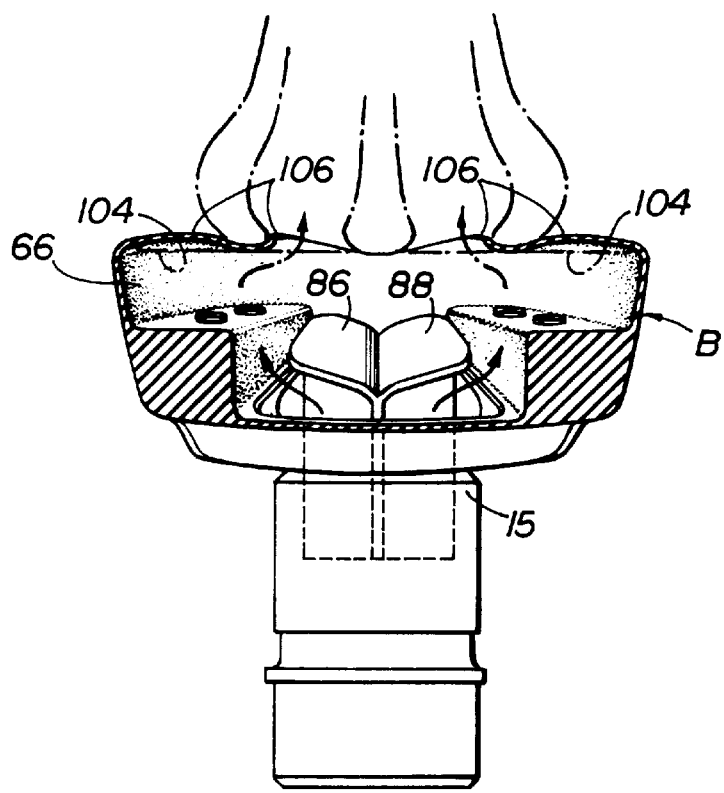
FIG. 7 is a view taken along line 7—7 of FIG. 6 illustrating the pre and post inflation of the nare seal according to the present invention.

As shown in FIGS. 5, 5A and 7, nare seal 14 has a first uninflated position illustrated by broken lines 104 when gas is not being provided to the patient. In the first uninflated position, top surface 56 rests against the bottom of the patient's nose and rearward surface 58 rests against the upper lip of the patient. When gas is being provided, nare seal 14 has a second inflated position illustrated by solid lines 106 wherein top surface 56 deflects upward and rearward surface 58 deflects rearwardly against the patient's upper lip to encircle the patient's nares and seal the area surrounding the patient's nares.

As further shown in FIGS. 3 and 4, nare seal support 15 includes support arms 16 and 18 and central support 17. Preferably, nare seal support 15 is formed from an integral unitary plastic piece wherein support arms 16 and 18 extend outward from central support 17 for engaging the face of the patient preferably at the cheek bones and ultimately for connecting with headgear assembly C. Support arms 16 and 18 are configured for transferring the force required to maintain nare seal 14 in a sealed orientation with the patient's nares to the cheekbones of the patient. Support arms 16 and 18 are mirror images of one another. Support arm 16 includes a first portion 108 which extends rearwardly from central support 17 a general distance and deflects at an obtuse angle at deflection point 110. Second portion 112 of support arm 16 continues rearwardly from deflection point 110 and terminates at distal end 114. Second portion 112 has a curved interior surface for matingly contouring with a patient's face. A respective of contact connector 48 is carried by the exterior of distal end 114. Distal end 114 includes an interior surface which is convex for positioning contact connector 48 generally perpendicular to contact connector located at first depending arm 30. A first facial pad 116 is carried by the interior of support arm 16 for contact with a patient's face. Support arm 18 being a mirror image of support arm 16 has similar components such as first portion 118, deflection point 120, second portion 122, distal end 124 and contact connector 46.

Thus, it can be seen that an advantageous construction of a nasal mask and headgear assembly may be had according to the invention. The small profile of the nare seal provides sufficient sealing for maintaining positive pressure within the airway of the patient while minimizing intrusion onto the face of the patient providing for a comfortable sleeping environment. The headgear assembly, in combination with the contact connectors, enables the nare seal to be quickly and easily attached and detached should the patient need to remove the mask upon waking during the sleep period as well as reattached for subsequent sleeping. The lateral arms of the mask support removes any supporting force from the patient's nose and positions the force onto a bone structure which is more suitable for supporting the nare seal.

While a preferred embodiment of the invention has been described using specific terms, such description is for illustrative purposes only, and once the innovative features of the invention are known, it is to be understood that changes and variations may be made without departing from the spirit or scope of the following claims:

What is claimed is:

1. A nasal mask assembly for providing gas from a gas source to a patient comprising:
   (1) a nasal mask comprising:
      (a) a nare seal having a surface for encircling nares of a patient, said nare seal defining a gas opening permitting gas from a gas source to enter nares of a patient, said nare seal being sized so as to minimize a contact area between said nare seal and a nasal area of a patient, and
      (b) a nare seal support carrying said nare seal, said nare seal support including:
         a central support portion supporting said nare seal,
         a first lateral arm having a first end operatively coupled to a first side of said central support portion, a second end, and a first attachment portion at said second end of said first lateral arm,
         a second lateral arm having a first end operatively coupled to a second side of said central support portion, a second end, and a second attachment portion at said second end of said second lateral arm,
         said first lateral arm including a first lateral arm connector disposed at said attachment portion of said first lateral arm; and
         said second lateral arm including a second lateral arm connector disposed at said attachment portion of said first lateral arm; and
   (2) a head gear assembly comprising:
      (a) a first depending arm carrying a first connector, and
      (b) a second depending arm carrying a second connector, wherein said first lateral arm connector releaseably attaches said first lateral arm to said first depending arm and said second lateral arm connector releaseably attaches said second lateral arm to said second depending arm, wherein said first connector and said second connector releaseably attach to said first lateral arm connector and said second lateral arm connector, respectively, at various angles so that said nare support is selectively positionable at varying angles relative to a patient, thereby enabling said nare seal to be positioned at various positions for encircling nares of a patient.

2. A nasal mask assembly for providing gas from a gas source to a patient comprising:
   (1) a nare seal having a first surface adapted to engage a lower portion of a patient's nose and a second surface, said first and said second surfaces defining a nare seal interior, said nare seal being sized so as to minimize a contact area between said nare, seal and a nasal area of such a patient, said first surface having a first gas opening defined therein permitting gas flow between said nare seal interior and an airway of a patient, said second surface having a second gas opening defined therein permitting gas from a gas source to enter said nare seal interior, and wherein said nare seal interior includes a plurality of spatial regions;
   (2) a nare seal support carrying said nare seal, said nare seal support including:
      (a) a central support portion supporting said nare seal with said second surface of said nare seal operatively coupled to said central support portion,
      (b) a first lateral arm having a first end operatively coupled to a first side of said central support portion and a second end, and
      (c) a second lateral arm having a first end operatively coupled to a second side of said central support portion and a second end, and wherein said first lateral arm and said second lateral arm each include an attachment portion at said second end of each lateral arm on a second surface opposite said first surface to engage a headgear assembly for securing said nasal mask assembly to a head of patient; and
   (3) a gas distribution assembly interposed between a gas source and said nare seal interior, wherein said gas distribution assembly comprises a plurality of channels, each being adapted to distribute gas from such a gas source to one of said plurality of spatial regions in said nare seal interior so that gas entering said interior in a first direction from such a gas source is diverted in a second direction before entering a patient's nares, wherein said gas distribution assembly includes at least one flange disposed in a direction of travel of such gas so as to divert such gas from said first direction in said second direction.

* * * * *